US00PP22465P2

(12) United States Plant Patent
Brand et al.

(10) Patent No.: US PP22,465 P2
(45) Date of Patent: Jan. 24, 2012

(54) ***BUDDLEJA* PLANT NAMED 'SUMMER SKIES'**

(50) Latin Name: *Buddleja davidii*
Varietal Denomination: Summer Skies

(75) Inventors: Mark Henry Brand, Willington, CT (US); William Addison Smith, Eastford, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 12/804,186

(22) Filed: Jul. 15, 2010

(51) Int. Cl.
*A01H 5/00* (2006.01)

(52) U.S. Cl. ..... Plt./242

(58) Field of Classification Search ..... Plt./242
See application file for complete search history.

(56) References Cited

U.S. PATENT DOCUMENTS

| | | | |
|---|---|---|---|
| PP12,383 | P2 | 2/2002 | Dransfield |
| PP14,370 | P2 | 12/2003 | Turrell et al. |
| PP19,950 | P3 | 4/2009 | Werner et al. |
| PP19,991 | P3 | 5/2009 | Werner et al. |

*Primary Examiner* — June Hwu
*Assistant Examiner* — Louanne Krawczewicz Myers
(74) *Attorney, Agent, or Firm* — Kilpatrick Townsend & Stockton LLP

(57) ABSTRACT

*Buddleja davidii* 'Summer Skies' is a distinct form of butterfly bush that combines several desirable characteristics in a landscape plant including the following: upright and outwardly spreading plant habit; green and yellow to bright white leaf variegation with sharp contrast between colors; variegated foliage that is resistant to sun scald and greening; vigorous and free branching habit; long floral panicles of pale violet-blue flowers that are freely produced; easy asexual propagation by softwood or semi-hardwood cuttings; and rapid plant development in container culture.

3 Drawing Sheets

Latin name of the genus and species: Genus: *Buddleja.* Species: *davidii.*

Variety denomination: The inventive cultivar of *Buddleja davidii* disclosed herein has been given the variety denomination of 'Summer Skies'.

BACKGROUND OF THE INVENTION

The present invention relates to a new and distinct cultivar of *Buddleja,* botanically known as *Buddleja davidii,* and hereinafter referred to by the name 'Summer Skies'.

The new *Buddleja* was discovered and selected by the inventors as part of a larger mutant screen for phenotypically unique individuals at Storrs, Conn. in June, 2007. The mutant population was derived from chemical mutagenesis of the commonly available seed *Buddleja davidii* Assorted Colors (is a descriptor for a commonly sold type of seed that is comprised of seed from various cultivars), which is not patented. Ethylmethane sulfonate (EMS) was the chemical mutagen used according to standard protocols for seed mutagenesis. Seeds were imbibed overnight then treated for four hours in buffered EMS (200 millimolar). The mutagenized seeds were germinated and grown on under greenhouse conditions. 'Summer Skies' presented itself early on as a unique variegated mutant from over two thousand seedlings.

Asexual reproduction of 'Summer Skies' by cuttings has shown that the periclinal leaf variegation is stable and reproduced true-to-type in successive generations. The original plant was propagated asexually in late spring 2008 by softwood to semi-hardwood stem cuttings taken from greenhouse-grown materials at Storrs, Conn. Fifty cuttings were potted and evaluated out of doors under drip irrigation for one growth season. An additional five rooted stem cuttings were also grown under field conditions at Storrs, Conn. and evaluated over a three year period (2008 through 2010). Following their first growing season, the original fifty plants propagated were distributed in early summer of 2009 to test locations and evaluated for ease of asexual propagation, stability of the variegation and landscape performance. These test locations included controlled environments in Lebanon and Hamden, Conn., Grand Haven, Mich. and Pensacola, Fla. It was found that 'Summer Skies' was easily propagated by stem cuttings. During all asexual propagation, the characteristics of the original plant have been maintained. Plants derived from stem cuttings exhibit characteristics identical to those of the original plant.

Cuttings may be taken from June through August from field-grown materials, however greenhouse-grown materials root readily throughout the year. Nearly 100% of cuttings root and produce profuse root systems under intermittent mist in 7 to 10 days with the application of rooting hormone (1000 parts per million indole-3-butyric acid). Cuttings rooted by early summer may be grown to 2 gallon container size in one growing season. Vigorous, highly floriferous plants can be marketed by the second growing season following over-wintering dormancy and pruning.

SUMMARY OF THE INVENTION

The following traits have been repeatedly observed and are determined to be the unique characteristics of 'Summer Skies'. The characteristics below, in combination, distinguish 'Summer Skies' as a new and distinct cultivar.

1. Upright and outwardly spreading plant habit.
2. Green and yellow to bright white leaf variegation with sharp contrast between colors.

3. Variegated foliage is resistant to sun scald and "greening".
4. Vigorous and free branching habit.
5. Long floral panicles of pale violet-blue flowers are freely produced.
6. Easy asexual propagation by softwood or semi-hardwood cuttings.
7. Rapid plant development in container culture.

This stable periclinal variegated selection was named *Buddleja davidii* 'Summer Skies' because of its bright white variegation, which appears cloud-like from a distance, and its pale colored violet-blue flowers that are reminiscent of blue sky. Mature leaves of 'Summer Skies' are lanceolate in shape and about 12 cm long by 4 cm wide for leaves three to six nodes below the terminal panicles. Leaf tips are acuminate, leaf bases are acute and leaf margins are serrate. The leaves are distinctly variegated with approximately 60-80% of the central portion of the leaf a mid-dark green (RHS 137A) with minor sectoring of a pale green (RHS 147B) at the marginal interface. The leaf margin is bright yellow (RHS 7A) under greenhouse conditions, but is more yellow-white (RHS 158B) under full sun conditions. Color references as used herein are made to The Royal Horticultural Society Colour Chart (R.H.S.), 1987 edition, except where general colors of ordinary significance are used. 'Summer Skies' has green and yellow to bright white leaf variegation with sharp contrast between colors. The variegated foliage of 'Summer Skies' distinguishes it from the paternal *Buddleja davidii* varieties, which have green leaves that are not variegated.

The overall appearance of the plant is distinctly white from a distance and is different from the variegation of the cultivar 'Santana' U.S. Plant Pat. No. 12,383, which is not as notably white from a distance. The yellow-white leaf margin of 'Summer Skies' (5-10 mm) is also significantly broader than another variegated cultivar, 'Harlequin', not patented, which has much narrower white leaf margins (2-3 mm). The panicles of 'Summer Skies' are quite long with initial terminal panicles exceeding 45 cm long by 6.5 cm wide and secondary lateral panicles approximately 35 cm×6 cm. The panicle color is a light violet-blue (RHS 85A for newly opened flowers turning bluer RHS 85B as the flowers mature) which complements well with the foliage.

BRIEF DESCRIPTION OF THE PHOTOGRAPHS

The accompanying photographs illustrate the typical foliage, flowers, plant habit and overall appearance of 'Summer Skies', showing the colors as true as is reasonably possible with colored reproductions of this type. Colors in the photographs may differ slightly from the color values cited in the detailed botanical description, which accurately describe the color of 'Summer Skies'.

DETAILED BOTANICAL DESCRIPTION OF THE VARIETY

Figure 1:
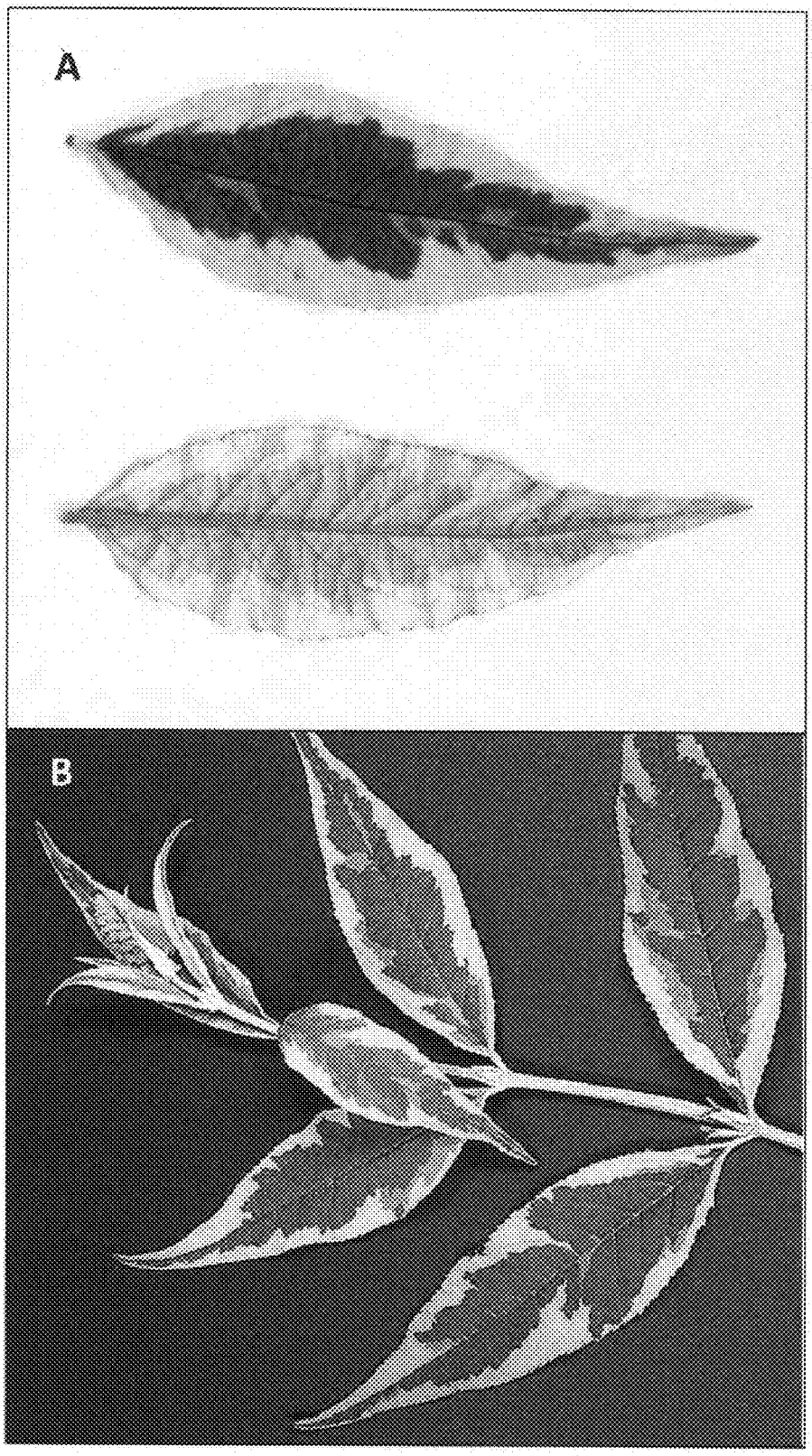
FIG. 1 shows foliage variegation on greenhouse-grown plants illustrating mid-dark green central leaf portions surrounded by yellow margins with some overlapping green and yellow tissue layers at the interface, where panel A shows adaxial (top) and abaxial (bottom) leaf surfaces, and panel B shows a shoot tip with a few nodes and associated opposite leaves.
Figure 2:
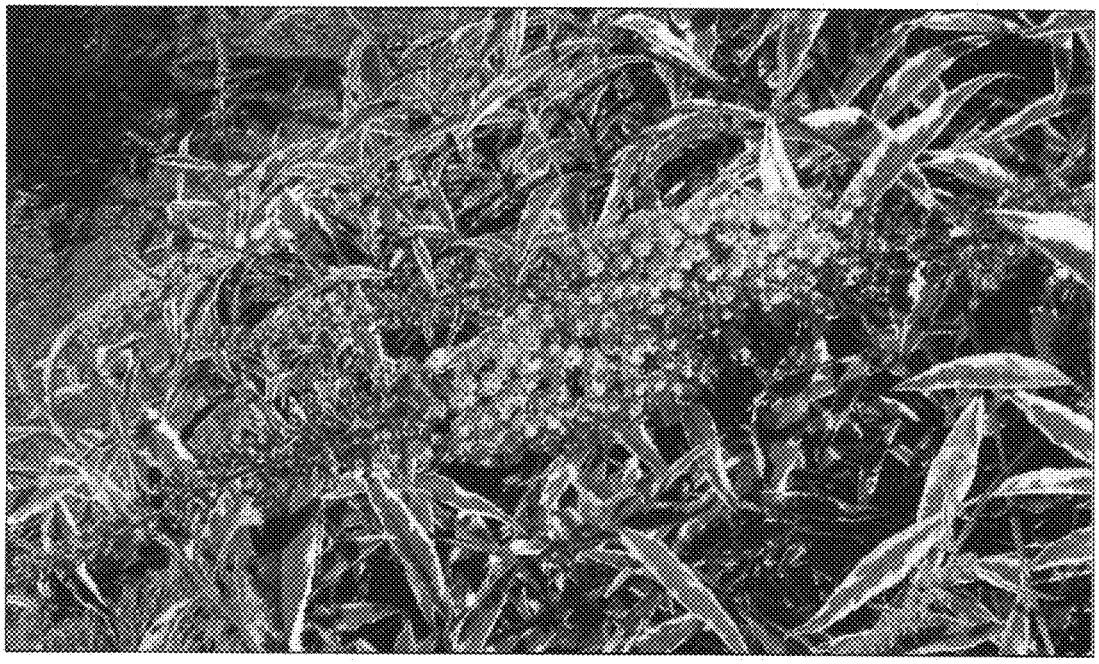
FIG. 2 shows half opened panicles illustrating pale violet-blue color and long, tapered panicle shape.
Figure 3:
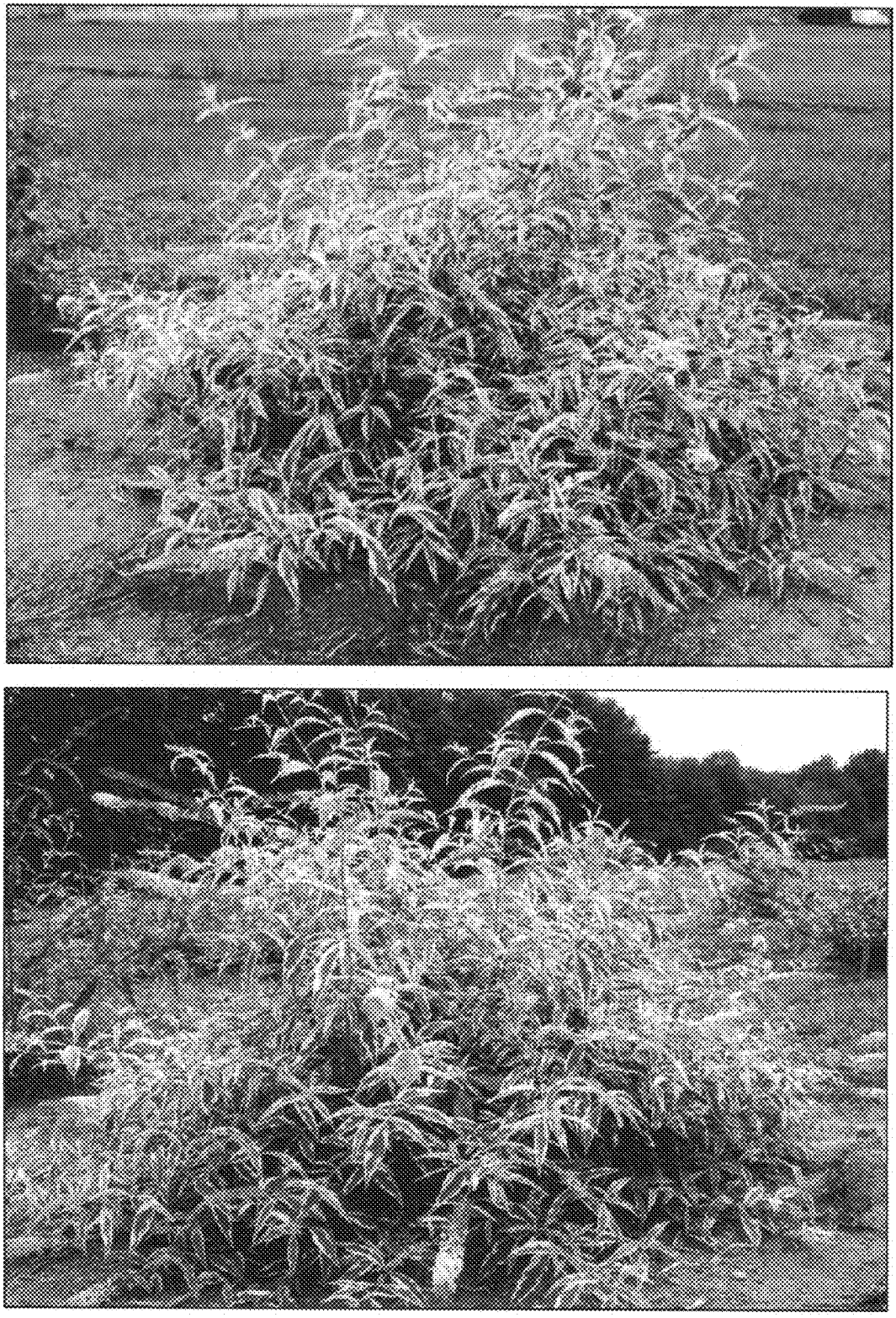
FIG. 3 (upper and lower panels) shows the typical habit and appearance of plants grown in full sun exposure by mid- to late summer; plants are about 1.5 meters tall and 1.2 meters wide.

The following is a detailed description of the botanical and ornamental characteristics of the subject *Buddleja davidii* 'Summer Skies' as grown throughout the summer of 2008 and 2009 at the inventors' location (Storrs, Conn.) grown under field conditions. Principle descriptions were obtained while the plants were in full bloom in mid-August. Color data are based on The Royal Horticultural Society Colour Chart, The Royal Horticultural Society, London, 1987 edition. Where dimensions, sizes, colors and other characteristics are given, it is to be understood that such characteristics are approximations of averages set forth accurately as practicable. The descriptions reported herein are from two-year-old specimens.

Genus: *Buddleja.*
Species: *davidii.*
Denomination: 'Summer Skies'.
Commercial classification: Shrub or sub-shrub; deciduous.
Common name: Butterfly bush.
Type: Ornamental.
Uses: Herbaceous perennial border or shrub border for residential or commercial landscapes.
Cultural requirements: Full sun exposure, well-drained soil, and moderate moisture.
Parentage: Chemical mutagenesis of open pollinated seeds of unknown parentage.
Plant description:

*Bloom period.*—Mid-summer to early fall until frost.
*Blooming habit.*—Slightly drooping, long panicles.
*Vigor.*—Moderately vigorous.
*Plant habit.*—Upright and outwardly spreading plant habit; fairly dense.
*Height and spread.*—1.5 meters (height) and 1.2 meters (width).
*Branching habit.*—Freely branching.
*Hardiness.*—To date, hardy to minus 14 degrees Centigrade. Not tested below this temperature. Anticipate plant will be adapted for USDA hardiness zones 5-9.
*Propagation.*—Softwood to semi-hardwood cuttings under intermittent mist. Roots typically in less than 2 weeks.
*Root system.*—Fibrous.
*Seasonal interest.*—Bright yellow to white variegated foliage throughout the growing season. Long panicles of pale violet-blue flowers in July, August, September.
*Disease and pest susceptibility and resistance.*—No particular susceptibility or resistance, except occasionally susceptible to spider mites under very hot and dry conditions as is typical for the species.
*Special growing requirements.*—Severe annual pruning in late winter or early spring prior to bud break is recommended to encourage strong regrowth and more profuse flowering.

Stems:

*Shape.*—Stem cross section is quadrangular.
*Length.*—Average 120 cm with maximum 140 cm noted.

*Color.*—Pale-green (RHS 139D) on recently formed shoots.
*Diameter.*—4 mm near terminal portion of stem, and 20 mm near base of stem.
*Stem surface.*—Glaucous.
*Pubescence.*—Absent.
*Internode length.*—6-7 cm between nodes.

Foliage:
*Type.*—Deciduous.
*Leaf arrangement.*—Opposite, decussate.
*Leaf division.*—Simple.
*Leaf shape.*—Lanceolate.
*Leaf base.*—Attenuate.
*Leaf apex.*—Acuminate.
*Leaf venation.*—Pinnate.
*Leaf surface* (*adaxial*).—Glaucous.
*Leaf surface* (*abaxial*).—Pubescent.
*Leaf margin.*—Serrulate.
*Leaf attachment.*—Petiolate.
*Petiole dimensions.*—5 mm in length; 2 mm in width.
*Petiole shape.*—Sulcate.
*Petiole color.*—Pale-green (RHS 139D).
*Leaf color.*—Adaxial side distinctly variegated with approximately 60-80% of the central portion of the leaf a mid-dark green (RHS 137A) with minor sectoring of a paler green (RHS 147B). The leaf margin is bright yellow (RHS 7A) under greenhouse conditions but fades to bright yellow-white (RHS 158B) under full sun. Abaxial side leaf color is 158B on the abaxial leaf margin and the abaxial central portions of the leaves are 198B.
*Leaf length.*—Average length (10 leaves three to six nodes from terminal panicle)=12 cm.
*Leaf width.*—Average width (10 leaves three to six nodes from terminal panicle)=4 cm.
*Foliar fragrance.*—None detectable.

Flowers:
*Inflorescence.*—Terminal and axillary panicles.
*Petals.*—4 in number.
*Fused or unfused.*—Fused at base.
*Petal margin.*—Entire.
*Petal apex.*—Rounded lobes, serrulate.
*Petal base.*—Truncate.
*Petal surface.*—Glaucous.
*Petal shape.*—Rotund.
*Petal dimensions.*—10 mm in length; 7 mm in width.
*Petal color.*—Adaxial and abaxial surface=newly opened flowers pale violet (RHS 85A) turning bluer (RHS 85B) as flowers mature.
*Flower shape.*—Salverform.
*Corolla tube color.*—Inside surface is red orange (RHS 34A) with a smaller eye than typical.
*Corolla tube surfaces* (*inner and outer surfaces*).—Pubescent.
*Corolla tube shape.*—Tubular.
*Color of penduncle.*—Pale-green (RHS 139D).
*Peduncle surface.*—Glaucous.
*Peduncle length.*—0.7 cm.
*Peduncle shape.*—Flattened oval in cross section.
*Pedicel dimensions.*—1.0-2.0 mm in length and less than 1 mm in diameter.
*Pedicel color.*—Pale green (RHS 139D).
*Pedicel shape.*—Flattened oval in cross section.
*Pedicel surface.*—Glaucous.
*Flowers persistent or self-cleaning.*—Flowers are persistent.
*Lastingness of the overall inflorescence.*—2-3 weeks.
*Lastingness of an individual flower.*—3-5 days.
*Dimensions of inflorescence.*—Initial terminal panicles are 46 cm long and 6.5 cm wide. Panicles derived from axillary branches are 35 cm long and 6 cm wide.
*Dimensions of entire individual flower.*—10 mm length; diameter 7 mm at apex, tapering to 1-2 mm at base.
*Quantity of flowers.*—Approximately 1200 flowers per individual inflorescence.
*Bud color.*—Pale green (RHS 145B).
*Bud apex.*—Rounded.
*Bud surface.*—Glabrous.
*Bud shape.*—Elongated, linear balloon.
*Bud length.*—10 mm long.
*Bud diameter.*—1-1.5 mm.
*Calyx shape.*—Tubular.
*Calyx dimensions.*—1.0 mm in width and 3.0 mm in length.
*Sepal.*—Four in number.
*Sepal shape.*—Lanceolate.
*Sepal apex.*—Acute.
*Sepal margin.*—Entire.
*Sepal surface.*—Glabrous.
*Sepal color* (*both adaxial and abaxial surfaces*).—Pale green (RHS 139D).
*Flower fragrance.*—Distinct sweet fragrance.

Reproductive organs:
*Stamens.*—Four, fused to inside of petals.
*Anther shape.*—Oblong.
*Anther dimensions.*—1 mm in length and 0.2 mm wide.
*Filament size.*—5 mm in length and less than 0.5 mm in width.
*Pollen amount.*—Typically high.
*Pollen color.*—Yellow-white (RHS 158D).
*Pistil.*—One in number.
*Pistil dimensions.*—Less than 1 mm in length, and less than 1 mm in diameter.
*Stigma color.*—Yellow-green (RHS 144A).
*Ovary.*—Present.
*Ovary position.*—Superior.
*Ovary shape.*—Oval.
*Fertility.*—Self-infertile; requires cross pollination; high fertility.

Fruit:
*Type.*—Elongated capsule.
*Dimensions.*—8.5 mm in length (variable) and 2.5 mm in diameter (variable).
*Color.*—Pale-green (RHS 139D) when immature.

That which is claimed:

1. A new and distinct variety of butterfly bush (*Buddleja davidii*) substantially as illustrated and described, characterized by its upright slightly spreading habit, exemplary leaf variegation and long fragrant blue-violet floral panicles.

* * * * *